(12) United States Patent
Cullum et al.

(10) Patent No.: US 7,256,886 B2
(45) Date of Patent: Aug. 14, 2007

(54) SURFACE ENHANCED RAMAN SPECTROSCOPIC NANO-IMAGING PROBE AND USES THEREFOR

(75) Inventors: Brian M. Cullum, Laurel, MD (US); Mikella Evon Hankus, Bel Air, MD (US); Nirmala Chandrasekharan, Baltimore, MD (US)

(73) Assignee: University of Maryland at Baltimore County, Baltimore, MD (US)

( * ) Notice: Subject to any disclaimer, the term of this patent is extended or adjusted under 35 U.S.C. 154(b) by 69 days.

(21) Appl. No.: 11/186,521

(22) Filed: Jul. 21, 2005

(65) Prior Publication Data
US 2006/0017917 A1   Jan. 26, 2006

Related U.S. Application Data

(60) Provisional application No. 60/590,277, filed on Jul. 22, 2004.

(51) Int. Cl.
*G01J 3/44* (2006.01)
*G01N 21/65* (2006.01)

(52) U.S. Cl. ...................................... 356/301; 385/116

(58) Field of Classification Search ................ 356/301; 385/116, 121
See application file for complete search history.

(56) References Cited

U.S. PATENT DOCUMENTS

| 5,633,972 A * | 5/1997 | Walt et al. ................... 385/116 |
| 7,012,687 B2 * | 3/2006 | Blumberg et al. .......... 356/301 |

* cited by examiner

*Primary Examiner*—F. L. Evans
(74) *Attorney, Agent, or Firm*—Benjamin Aaron Adler

(57) ABSTRACT

Provided herein is a reusable nano-imaging probe useful in surface enhanced Raman spectroscopic (SERS) applications demonstrating nanometer scale resolution. The nano-imaging probe generally comprises a fiber optic imaging bundle of fiber optic elements each having a tapered etched end and a non-tapered non-etched end. The tapered etched ends further comprise a SERS-active metal substrate deposited thereon effective to create a uniform SERS enhancement for an analyte or other substance of interest. Also provided is a SERS nanoimager for dynamic chemical imaging using the nano-imaging probe and methods of imaging and Raman spectral analysis and identification using the nano-imaging probe.

20 Claims, 10 Drawing Sheets

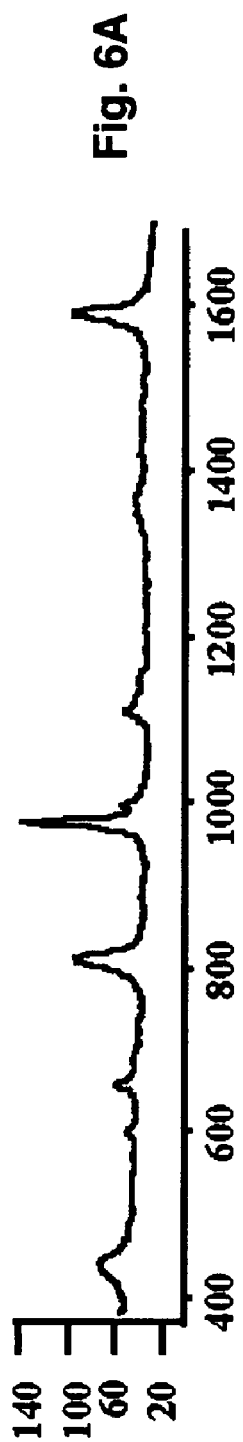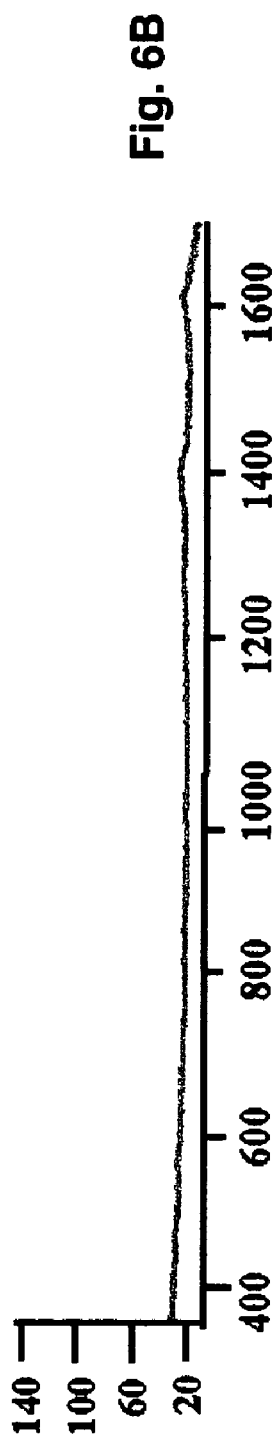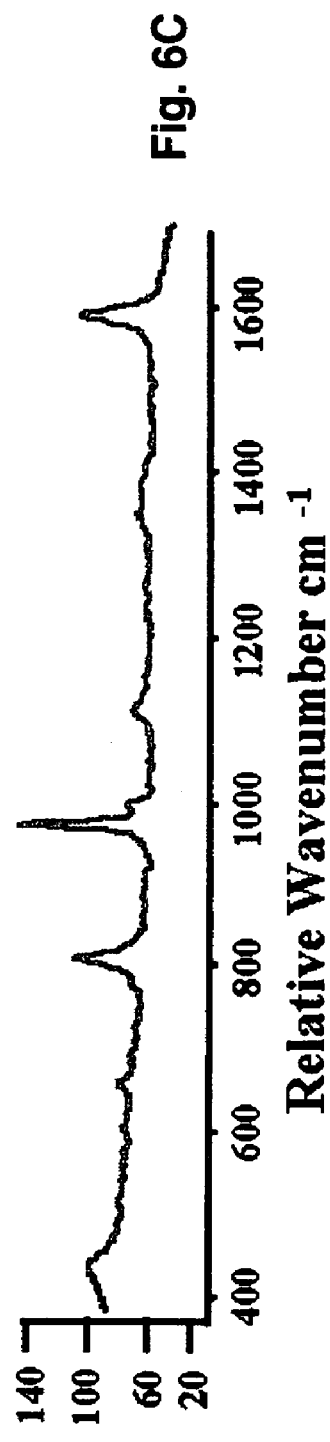

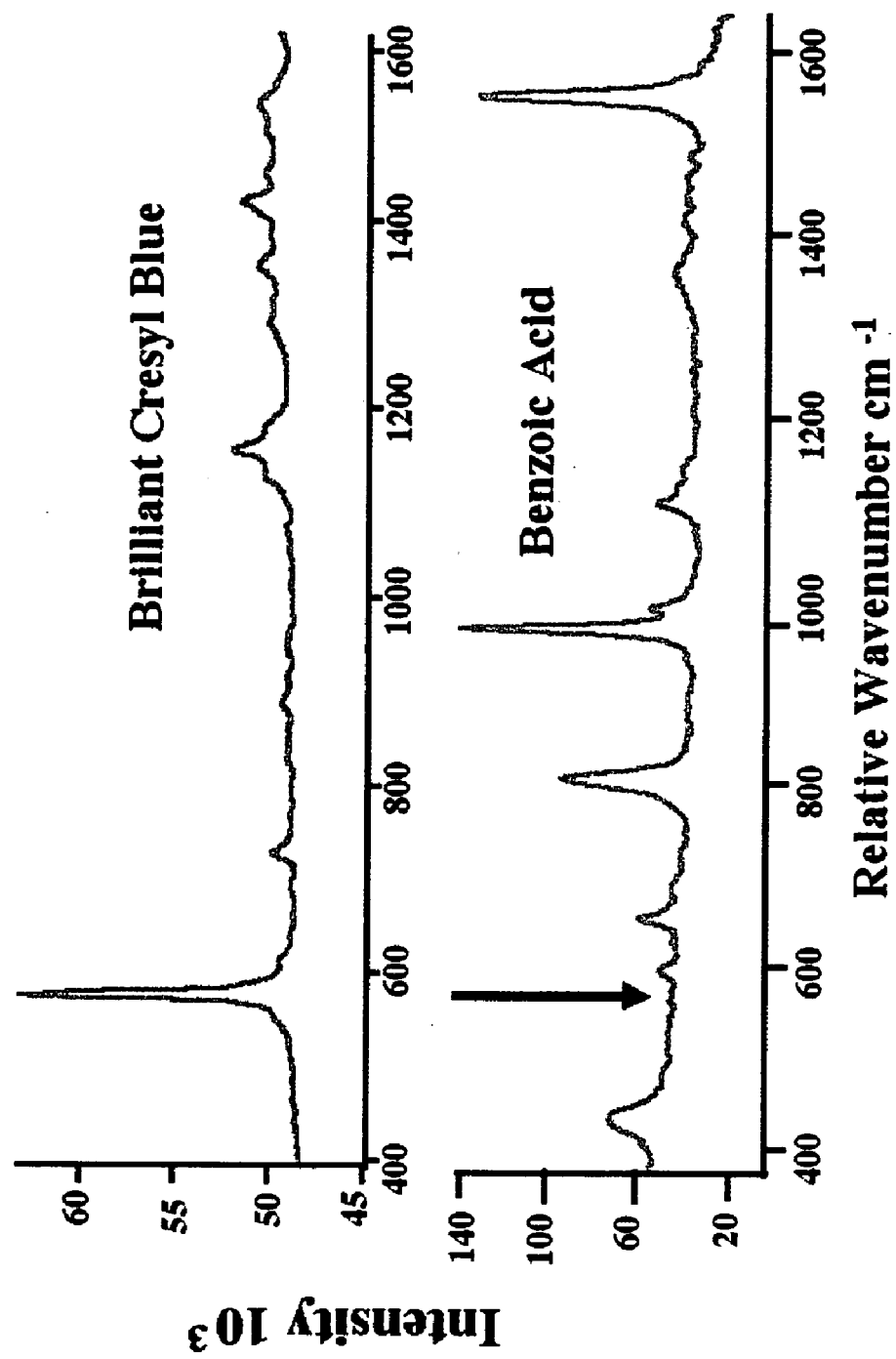

SURFACE ENHANCED RAMAN SPECTROSCOPIC NANO-IMAGING PROBE AND USES THEREFOR

CROSS-REFERENCE TO RELATED APPLICATION

This non-provisional application claims benefit of priority to provisional U.S. Ser. No. 60/590,277, filed Jul. 22, 2004, now abandoned.

BACKGROUND OF THE INVENTION

1. Field of the Invention

This invention relates generally to the fields of Raman spectroscopy and imaging. Specifically, the present invention relates to a nano-imaging probe useful in surface enhanced Raman spectroscopic applications.

2. Description of the Related Art

Recent technological advances in the controlled fabrication and manipulation of nanoscale systems and devices has generated increased interest in various nano-structures, both man-made, e.g., carbon nanotubes, (1-2) and naturally occurring, that is, biological cells or subcellular compartments (3). Synthesizing, characterizing and understanding such structures and their function, therefore, is extremely important to many fields ranging from drug delivery in the design of effective time-release materials (4-5) to space exploration in the fabrication of light-weight, rugged materials (6). In order to better characterize and further develop these nano-structures, the ability to visualize objects on the nanometer to hundreds of nanometer's scale is essential.

One area in which high-resolution imaging of individual chemical species will have a great impact is in biochemical studies. For example, a novel tool for characterizing dynamic intracellular and extracellular interactions on the nanoscale could offer insight into metabolic pathways, ion exchange mechanisms, and other essential cellular processes. In medical research, a tool for measuring and imaging localized chemical changes at the cellular and sub-cellular levels could allow for pre-symptomatic disease detection as well as potentially allow for the development of specific treatments for individuals (7-10).

Chemical imaging using optical spectroscopies has long been used for the identification and the determination of the spatial distribution of species within a sample. Using different optical spectroscopic techniques, i.e., fluorescence (11-13), Raman (14-18) and others (19-20), it is possible to obtain both qualitative, as well as quantitative, information about a sample. Fluorescence imaging is commonly used for the monitoring of trace amounts of a known analyte and Raman imaging is typically used for species identification. Recently, surface enhanced Raman spectroscopy (SERS) also has been employed for chemical imaging, providing both the qualitative identification of Raman imaging with the sensitivity necessary for trace analyses (21). However, the creation of uniform roughened metal surfaces, necessary for SERS, and thus uniform surface enhancement, is difficult to control from location-to-location which dramatically limits the use of SERS as an imaging technique (22-25). Additionally, the far-field imaging methodologies employed in conventional chemical imaging analyses ultimately limits the spatial resolution of such analyses to the diffraction limit of light, effectively preventing the imaging of nanometer scale objects.

To overcome this diffraction limited spatial resolution and to obtain chemical images with resolution on the nanometer scale, near-field chemical imaging techniques were developed, including near-field scanning optical microscopy (NSOM) (26-29). Coupling NSOM with the sensitivity of fluorescence spectroscopy, near-field chemical images of samples have been obtained for many different applications, including medical diagnostics (30), materials science studies (27,31) computer science (32) and chemical and biological research (33). More recently, the nanometer scale fiber optic tip used for scanning in most NSOM analyses was scanned over a SERS active surface to record SERS images with approximately 100 nm spatial resolution. This has resulted in the ability to visualize individual molecules, such as a single strand of DNA labeled with brilliant cresyl blue (BCB) (34-35).

While NSOM in conjunction with other spectroscopic techniques can be used to produce high-resolution chemical images below the diffraction limit of light, dynamic real-time sample imaging has not yet been feasible, as NSOM requires hours of scanning the probe tip across the surface (36). In addition, if a particular area of interest is found, it is often difficult to return to this exact location after the scan has been completed (36). Due to these limitations, NSOM is not particularly suited to studying dynamic chemical events.

Accordingly, a need is recognized in the art for improved surface enhanced Raman spectroscopic imagers useful for real time, reproducible imaging in a non-scanning format to overcome the challenge of SERS substrate reproducibility in SERS imaging and the dynamic limitation of NSOM. More specifically, the prior art is deficient in a SERS nanoimaging probe having a uniform, repeatable and regular nano-structured surface effective for nanoscale resolution and methods of making the same. The present invention fulfills this longstanding need and desire in the art.

SUMMARY OF THE INVENTION

The present invention is directed to a nano-imaging probe for a surface enhanced Raman spectrometer (SERS). The SERS nano-imaging probe comprises a fiber optic imaging bundle having a proximal flat tapered end and a distal flat non-tapered end. The imaging bundle includes a plurality of fiber optic elements, each of which has a tapered etched end surface at the proximal end adapted to uniformly contact an analyte and a flat non-tapered non-etched end surface at the distal end.

The present invention also is directed to a surface enhanced Raman spectroscopic nano-imager. The SERS nano-imager comprises a radiation source, the nano-imaging probe described herein, a detector for detecting Raman scattered radiation, a first set of optics for directing incident radiation from the source to the proximal end surfaces of the nano-imaging probe, and a second set of optics for directing Raman radiation emitted from the distal end surfaces of the nano-imaging probe to the detector. In a related invention the SERS nano-imager further may comprise means for analyzing and displaying the detected Raman scattered radiation as a Raman spectral image.

The present invention is directed further to a method for performing surface-enhanced Raman spectral analysis of an analyte. The method comprises providing the SERS nano-imaging probe described herein and bringing an analyte into effective contact with the nano-imaging probe. The molecules comprising the analyte are illuminated with radiation of a wavelength to produce Raman scattered radiation therefrom whereupon the Raman scattered radiation transmitted through said nano-imaging probe is collected for spectral analysis of the analyte. In a related invention the method further may comprise generating a signature spectrum for the analyte based on the spectral analysis. In another related invention the method further may comprise performing a surface-enhanced Raman spectral analysis on a sample to establish the presence of the analyte therein, such that, if the spectral signature of the sample matches the spectral signature of the analyte, the analyte is present in the sample.

The present invention is directed further still to a method of identifying one or more molecules in a sample in real time. The method comprises Iluminating a sample in effective contact with the nano-imaging probe described herein with radiation of a wavelength to produce Raman scattered radiation from one of the molecules and detecting the Raman scattered radiation. If the scattered radiation exhibits a known Raman spectral signature of the molecule, the molecule is identified as being in the sample. The method steps are repeated using a different illuminating wavelength for each molecule to be identified. An immediate comparison of Raman spectral signatures identifies the one or more molecules in real time.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A is a schematic of a cross-sectional view of the SERS nano-imaging probe showing the component parts. FIGS. 1B-1C show microscope images of a tapered fiber optic probe as shown perpendicular (FIG. 1B) to the microscope stage and parallel viewing the non-tapered end (FIG. 1C). The tapered flat surface prevents warping of images through the fiber bundle. FIG. 1D is a schematic of the SERS nanoimaging system.

FIG. 2A is a SEM image of a tapered probe tip showing uniformly hexagonal packed elements of 500 nm diameter. FIG. 2B is a tapered probe imaged at a 71° angle showing where HF acid has etched out the image transmission area, leaving a surrounding silica cladding and a surface of repeatable peaks.

In FIG. 3A a different single fiber element is illuminated in microscope image. In FIG. 3B surrounding fiber optic elements are illuminated with center element darkened, thus demonstrating that cross-talk is not occurring.

FIGS. 6A-6C demonstrate SERS nanoimaging probe reuseability. FIG. 6A depicts the spectra of benzoic acid on a SERS nanoimaging probe with the peak at 1002 $cm^{-1}$ and a S/N ratio of 260. In FIG. 6B the probe tip was washed in water and imaged. FIG. 6C depicts the final benzoic acid spectrum after 5 repeated washings and reapplication of benzoic acid to the probe and the benzoic acid reapplied. The S/N ratio is 264.

FIGS. 7A-7D demonstrate the ability of these probes to differentiate between chemical species brilliant cresyl blue and benzoic acid. Images of SERS nanoimaging probe coated with brilliant cresyl blue (FIG. 7A) followed by wash with benzoic acid (FIG. 7B) imaged at 580 $cm^{-1}$ wavenumber. The 580 $cm^{-1}$ wavenumber peak corresponds with the major brilliant cresyl blue peak (FIG. 7C), and not with any peaks of benzoic acid (FIG. 7D).

DETAILED DESCRIPTION OF THE INVENTION

Figure 1A:
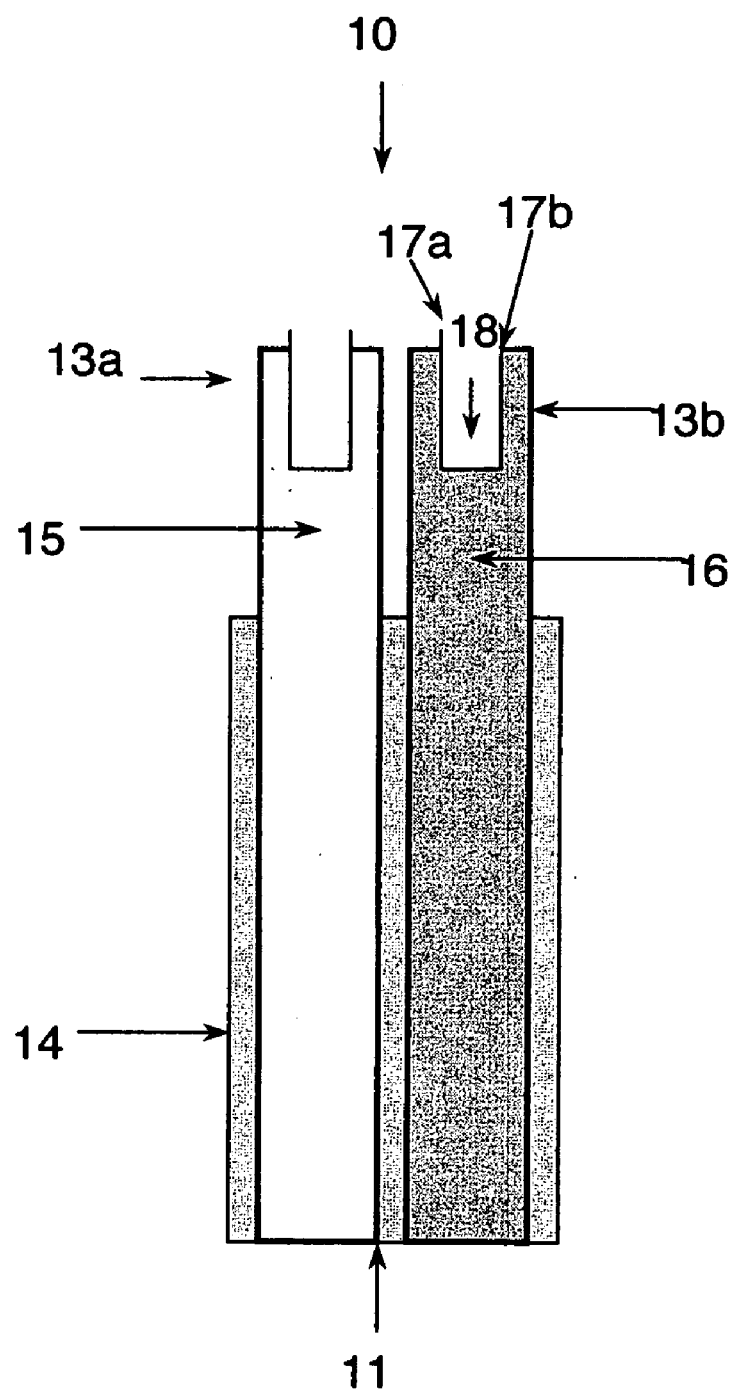
FIGS. 1A-1D depict the SERS nano-imaging probe and a surface enhanced Raman spectroscopic nanoimaging system.

In one embodiment of the present invention there is provided a nano-imaging probe for a surface enhanced Raman spectrometer, comprising a fiber optic imaging bundle having a proximal flat tapered end and a distal flat non-tapered end, the imaging bundle including a plurality of fiber optic elements, each of the fiber optic elements having a tapered etched end surface at the proximal end adapted to uniformly contact an analyte and a flat non-tapered non-etched end surface at the distal end.

In this embodiment the fiber optic elements comprise a core material and a cladding material surrounding the core material where the core and cladding materials are etched at the proximal tapered end surface thereby forming uniform cladding spikes around the etched core material. Further to this embodiment the cladding spikes may comprise a metal substrate deposited thereon. Examples of metals so deposited are silver, gold, platinum, copper, ruthenium, rhodium, or iron.

In these embodiments the core material may be germanium (IV) oxide or silicon dioxide. Also, in these embodiments, the cladding material may comprise fluorine containing silica, pure silica, fluoropolymers, or polymethylmethacrylate. Furthermore, the plurality of fiber optic elements may be about 100 to about 30,000.

In one aspect of these embodiments the proximal flat tapered end of the fiber optic imaging bundle may have a diameter of about 160 microns. In another aspect each tapered, etched fiber optic element end surface may have an identical diameter of about 10 nm to about 1000 nm. In all aspects of these embodiments each non-tapered, non-etched fiber optic element end surface has an identical diameter of about 100 nm to about 4 microns.

In another embodiment of the present invention there is provided a surface enhanced Raman spectroscopic nano-imager, comprising a radiation source; the nano-imaging probe described supra; a detector for detecting Raman scattered radiation; a first set of optics for directing incident radiation from the source to the proximal end surfaces of the nano-imaging probe; a second set of optics for directing Raman radiation emitted from the distal end surfaces of the nano-imaging probe to said detector. Further to this embodiment the nano-imager may comprise means for analyzing and displaying the detected Raman scattered radiation as a Raman spectral image.

In these embodiments the radiation source may be a laser. Also in these embodiments the detector may be a charge coupled device, an intensified charge coupled device or a digital camera. Furthermore, in these embodiments the first set of optics may comprise at least one filter operably disposed between the radiation source and the nano-imaging probe. In addition the second set of optics may comprise means to collimate SERS radiation and one or more filters operably disposed between the nano-imaging probe and the detector.

In yet another embodiment of the present invention there is provided a method for performing surface-enhanced Raman spectral analysis of an analyte, comprising providing the SERS nano-imaging probe described supra; bringing an analyte into effective contact with the nano-imaging probe; illuminating molecules comprising the analyte with radiation of a wavelength to produce Raman scattered radiation therefrom; and collecting the Raman scattered radiation transmitted through the nano-imaging probe for spectral analysis of the analyte.

Further to this embodiment the method comprises generating a signature spectrum for the analyte based on the spectral analysis. In another further embodiment the method comprises performing a surface-enhanced Raman spectral analysis on a sample to establish the presence of the analyte therein, where, if the spectral signature of the sample matches the spectral signature of the analyte, the analyte is present in the sample.

In still another embodiment of the present invention there is provided a method of identifying one or more molecules in a sample in real time, comprising illuminating a sample in effective contact with the nano-imaging probe described herein with radiation of a wavelength to produce Raman scattered radiation from one of the molecules; detecting the Raman scattered radiation; determining that the scattered radiation exhibits a known Raman spectral signature of the molecule thereby identifying the molecule in the sample; and repeating the method steps with a different illuminating wavelength for each molecule to be identified, wherein an immediate comparison of Raman spectral signatures identifies the one or more molecules in real time.

The present invention provides a SERS-based nanoimaging probe capable of chemical imaging with nanometer scale spatial resolution. These SERS fiber optic based probes are capable of obtaining measurements at numerous locations simultaneously with nanoscale resolution. The SERS probe combines the qualitative and quantitative information provided by SERS spectroscopy with imaging technologies thus providing methodologies for discriminating between analytes and for identifying spatial distribution and movement of various biochemical species within cellular environments.

Figure 1B:
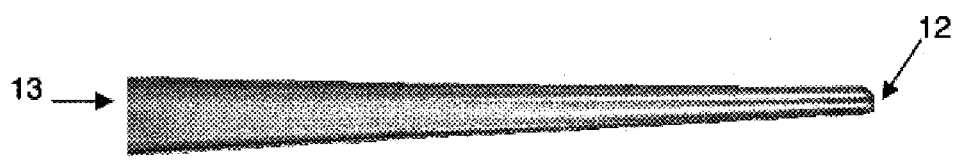
Figure 1C:
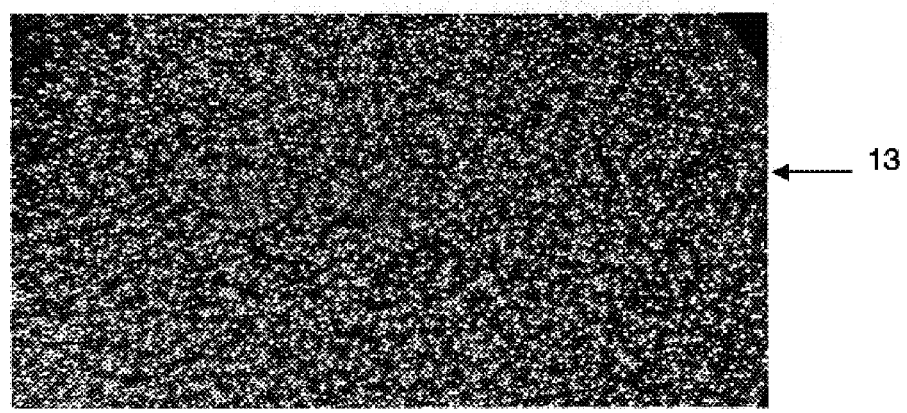

FIG. 1A is a cartoon depiction of the arrangement and construction of two representative fiber optic elements in an imaging bundle. It is noted that all elements in the imaging bundle have cladding, however for the purposes of demonstration one of the fiber elements shows the core without the cladding. It should be construed that any feature identified on one or the other element is present on all fiber optic elements comprising the imaging bundle. FIGS. 1B-1C are actual SEM images of the flat tapered and flat nontapered ends of the imaging bundle.

Generally, with reference to FIGS. 1A-1C, the SERS nanoimaging probe 10 is fabricated on a coherent fiber optic imaging bundle 11 to have a proximal modified flat, tapered end 12, as actually depicted in FIG. 1B, and a flat non-tapered distal end 13, as actually depicted from different views in FIG. 1B-1C. The tapered diameters may range from tens of nanometers to micrometer size. Generally the diameter is determined by the size of the imaging bundle used as well as the potential application of the SERS nanoimaging probe. For example, in an imaging bundle comprising about 30,000 individual fiber optic elements, the modified flat, tapered end 12 may have a diameter of about 160 microns.

The imaging bundle 11 has a plurality of individual light transmission fiber optic elements two of which 13a,b are depicted schematically in FIG. 1A. The actual bundle of fiber optic elements is shown in FIG. 1C. An imaging bundle may comprise about 100 to about 30,000 individual fiber optic elements. The fiber optic imaging bundle 11 has an outer jacket 14 covering the bundled fiber optic elements 13a,b from the distal end up to, but not including, the tapered proximal end 12. Imaging bundles used to fabricate the SERS nano-imaging probe is commercially available.

Each fiber optic element within the imaging bundle 11 has a core 15, as depicted by 13b, surrounded by a cladding 16. In general, the core material may comprise a wide variety of materials such as those used in optical fibers and in waveguide development. For example the core may be, but not limited to, a germanium (IV) oxide core, $GeO_2$, or silicon dioxide $SiO_2$. The cladding may be any material used for coherent fiber optic image bundle fabrication, such as, but not limited to, a fluorine containing silica, pure silica, fluoropolymers, or polymethylmethacrylate (PMMA). Each fiber optic element is tapered at the proximal end so that each proximal end surface has an identical diameter. Fiber element diameters may range from about 10 nm to about 1000 nm. The fiber optic elements each have an identical distal non-tapered end surface diameter of about 100 nm to about 4 microns. The cladding 16 and the core 15 are acid etched using well-known etchants, for example, with hydrofluoric acid (HF) or ammonium fluoride, to form cladding spikes, two of which are depicted at 17a,b around an etched cores 18.

Figure 2A:
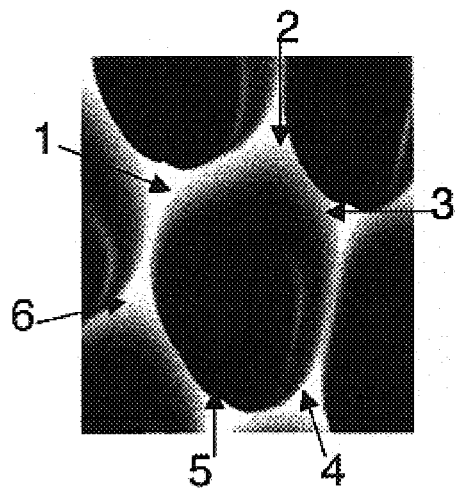
FIGS. 2A-2B show a SERS nano-imaging probe created using micropipette puller and HF etching.
Figure 2B:
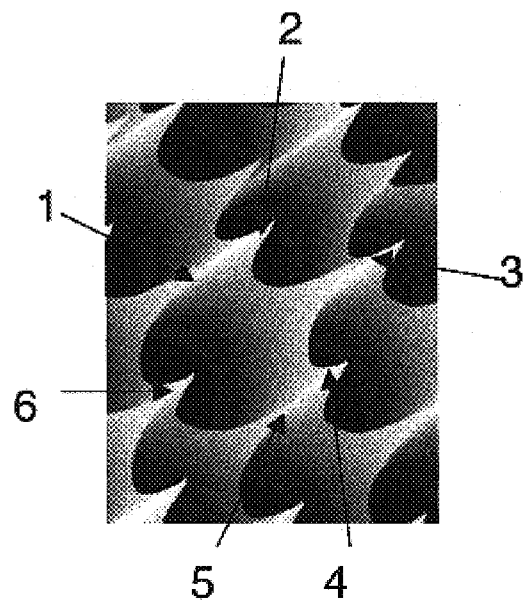

As actually depicted in FIGS. 2A-2B, the etched cores have a hexagonal shape with six cladding spikes as depicted at positions 1,2,3,4,5,6, formed around an etched core. A SERS-active metal substrate layer is formed on each cladding spike by metal deposition using known techniques, such as, but not limited to, evaporation or sputtering. The metal substrate layer may be a silver, gold, platinum, copper ruthenium, rhodium, or iron substrate. This forms a highly reproducible SERS surface.

Also provided herein is a SERS nanoimager utilizing the SERS nano-imaging probe. The nanoimager comprises a radiation source, the SERS nano-imaging probe, a detector, optics to direct radiation from the radiation source to the probe and from the probe to the detector. The nanoimager further may comprise the hardware and software necessary to display the spectral signature of a compound or analyte.

Generally, the radiation source may be a laser emitting radiation in the UV to the IR range or any other suitable excitation source for SERS analysis. Some examples of common, commercially available lasers include argon ion lasers emitting wavelengths of 448 nm or 514.5 nm, krypton ion lasers emitting wavelengths of 530.9 nm or 647.1 nm, HeNe lasers emitting wavelength of 632.8 nm, diode lasers emitting wavelengths of 782 nm or 830 nm, or Nd/YAG lasers for wavelengths of 1064 nm. Commercially available detectors may be charge coupled devices or digital cameras. The optics, also commercially available, may comprise one or more filters or other optical devices effective to filter or select radiation of particular wavelengths or to collect and collimate Raman scattered photons or radiation. These components are well-known and standard in the art of Raman spectroscopy.

Figure 1D:
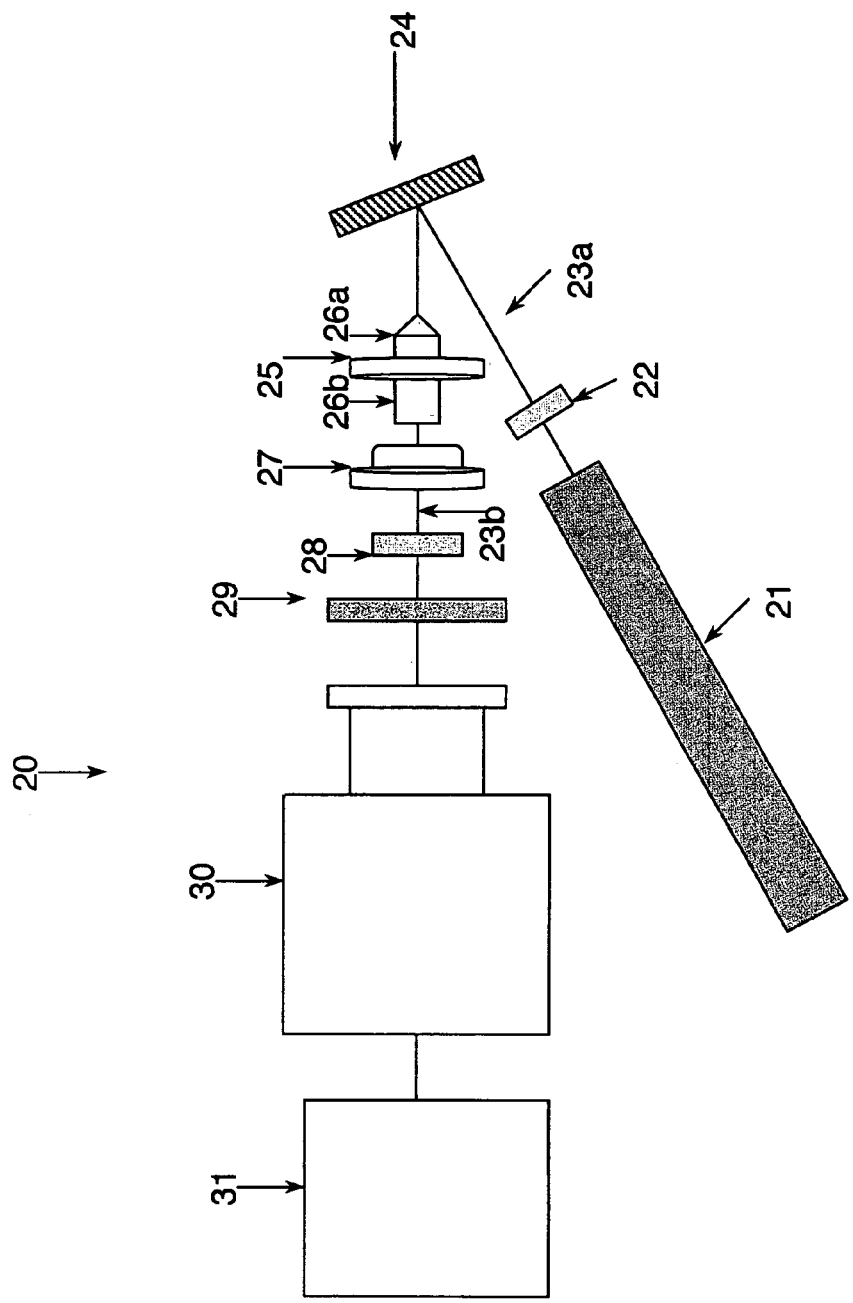

The nanoimager system 20 used to obtain SERS images is shown in FIG. 1D. A 22.5 mW CW HeNe laser 21 operates at 632.8 nm and the emitted radiation is filtered by a band-pass filter 22 to remove any possible plasma emission lines. The filtered laser line 23a is reflected by a mirror 24 onto the tapered and silvered sample end 26a of the nano-imaging probe 25. The scattered SERS photons are transmitted through their adjacent fiber elements in the bundle to the untapered end 26b where the transmitted light is collimated with a 4× microscope objective 27.

The collimated beam 23b is passed through a holographic notch filter 28 to reject any Rayleigh scatter present and is filtered further with an acousto-optic tunable filter 29 (AOTF) used to select specific wavelengths of interest. One example of an AOTF has a 7.5 $cm^{-1}$ spectral resolution, allowing for high resolution chemical discrimination as well as rapid tuning between wavelengths. Resulting SERS images from the nano-imaging probe 25 were collected and imaged onto a thermoelectrically cooled intensified charge coupled device 30 (ICCD) with a zoom lens. It is contemplated that the detector also may be a simple charge coupled device or a digital camera. Images are collected by the ICCD 30 and are viewed on the computer display 31. In order to evaluate SERS images obtained using the SERS nano-imager, data maybe analyzed using any image analysis software, e.g., ImageJ Winspec32 or ImagePro.

The present invention further provides methods utilizing the SERS nano-imaging probe and SERS nano-imager described herein to perform a spectral analysis to generate a signature spectrum of an analyte that can be brought into effective contact therewith. Furthermore, the probe and nano-imager are useful to identify and characterize an analyte or the presence, interactions or distribution of an analyte in a substance such as comprises a biological structure like a cell. This provides fast real time analysis and identification with nanoscale accuracy.

Thus, it is contemplated that the SERS nanoimaging probe is useful in, but not limited to, the fields of medicine, food science, materials science, or engineering. For instance, in medicine, the ability to monitor cells and their interactions with other materials could offer insight into different disease pathways, metabolic processes, ion exchange mechanisms, and other essential biological processes. In other fields the SERS nanoimaging probe could be useful in maintaining quality control of products, for example, by detecting the presence and location of contaminants in situ.

The following examples are given for the purpose of illustrating various embodiments of the invention and are not meant to limit the present invention in any fashion.

EXAMPLE 1

Fabrication of Tapered Fiber Optic Imaging Bundle

Both ends of a 3-inch section of fiber optic imaging bundle are polished smooth using lapping paper. A one-inch section of protective jacket is removed from the center of the fiber bundle through mechanical processes, e.g., removal with a razor blade. The polished and jacket-stripped fiber is then suspended between the two tension mount clamps of a $CO_2$ laser based micropipette puller (Sutter Instruments P-2000) and tapered. The micropipette puller utilizes a $CO_2$ laser to heat the fiber while a tension device pulls along the fiber axis. By varying the programmable pulling parameters, i.e., temperature, heat time, cooling delay time, and the force with which the tension mount clamps separate, flat, tapered probe tips of varying diameters are reproducibly created. As confirmed from SEM images of tapered bundles, an even heating throughout the entire bundle occurs, resulting in each fiber element being equally drawn. After being tapered to the desired size, a final pull occurs as the fiber cools, cleaving it into two individual pieces.

By tapering the fibers via this process, each piece has one large untapered end and one tapered end with a flat surface and equi-diameter fiber elements (FIGS. 1B-1C). This flat surface allows for even contact with the sample being probed and the uniform fiber element diameter ensures light collection from equi-area locations, preventing a warped or fun-house mirror effect in the transmitted image. Additionally, the difference in diameter, or area, of the fiber elements on each end of the tapered fiber bundle results in an inherent image magnification, with the magnified image on the larger untapered end capable of being imaged via conventional optics onto a charge coupled device, an intensified charge coupled device (ICCD) or digital camera.

EXAMPLE 2

Etching the Tapered Ends

SERS active surfaces are applied to the tapered tip of the fiber optic imaging bundle to provide the chemical differentiation and imaging capabilities to the fiber optic nano-imaging probes while overcoming the SERS enhancement reproducibility issues associated with SERS imaging. The cladding surrounding each of the individual fiber elements provides the uniformly patterned underlying surface roughness upon which metal vapor is deposited via vacuum evaporation. The tapered fiber tips are placed in a solution of hydrofluoric acid in a process similar to that used to create microwell arrays in untapered fiber optic bundles (37-40). Due to the small size of the tapered fibers and the minimal amount of material to be etched out of the cores of the individual fiber elements, the tapered tips of the fibers were only suspended in the 25% hydrofluoric acid (HF; Aldrich) in water solution for periods of time ranging from 2-7 minutes depending upon the size of the tapered tip and the amount of etching desired.

Using a 25% HF solution, the probes etch at a rate of approximately 0.15 µm/minute, creating uniformly roughened surfaces in the shape of hexagonally packed honeycombs with the core of the individual fiber elements forming indentations, as the core etches faster than the surrounding cladding material (FIG. 2A). Since the cladding surrounding each of the individual fiber elements also is etched by the same HF solution and the thickness of the cladding is slightly greater at the intersection between three fiber elements, this etching process creates a unique series of six spikes encircling each of the individual fiber elements on the probes tip. This can be seen in SEM images of an etched, tapered fiber bundle tip taken obtained at an angle of 71° relative to the surface (FIG. 2B).

EXAMPLE 3

Silver Deposition

Once the desired underlying probe roughness was achieved with HF etching, an overlayer of silver is deposited by evaporating 99.999% pure silver shot (Kurt. J. Lesker Company) using an Explorer™-14 (Denton Vacuum) vacuum evaporator. In this procedure, the etched probe is suspended 15 cm above a tungsten boat (R. D. Mathis Company) containing the evaporating silver. The probes are oriented with the etched tips facing down toward the silver below and at a slight angle. This angle ensures that the silver selectively deposits on the cladding spikes instead of the cores, thereby providing a highly ordered silver island-like SERS structure. The silver is deposited at a rate of 1.8 nm/s, under a pressure of $3.0 \times 10^{-6}$ Torr.

Monitoring of the amount of silver deposited is accomplished using a quartz crystal microbalance (Inficon XTM/2 film thickness monitor) mounted beside the sample holder in the vacuum chamber. By depositing silver in this method, and varying the amount deposited to correspond to the degree of tapering of the fiber bundle, accurate control over the metal nanoparticle size and spacing can be accomplished, allowing the SERS enhancements to be tuned and optimized for particular excitation wavelengths. Additionally, since the silver is deposited around the individual fiber element cores used to transmit the SERS signal, a high degree of SERS signal collection occurs, providing excellent signal-to-noise ratios when obtaining images.

EXAMPLE 4

Tapering Prevents Cross-talk Between Fiber Elements

An important consideration in tapering these fiber optic imaging bundles is cross-talk from fiber element to fiber element. Through the tapering process, as the diameter of the individual fiber elements decreases from 4 μm to nanometers or hundreds of nanometers, the cladding surrounding each of the individual fiber elements also becomes thinner until finally total internal reflection within each element breaks down and light from one element is transmitted to a surrounding element. In order to determine how small individual fiber elements could be tapered, prior to exhibiting cross-talk and thus image degradation, several tapered fiber optic tips of varying element diameters, ranging from 140-1000 nm, were examined.

Tapered fiber optic bundles were mounted on the stage of an inverted optical microscope equipped with differential interference contrast (DIC) optics with the large untapered end facing the objective and the tapered end facing upward towards the illumination source. Once in place, the untapered end of the fiber bundle was imaged onto a digital camera mounted on the microscope, allowing each of the individual fiber elements to be seen. A diffuser was placed between the fiber and the light source. This diffuser scattered the light prior to entering the individual fiber elements on the tapered end of the bundle, allowing certain fibers to be illuminated based on the acceptance angle of the tapered elements and the angle of the scattered light.

Figure 3A:
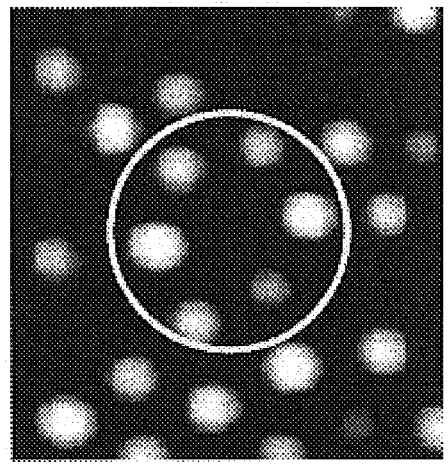
FIGS. 3A-3B depict microscope images of a tapered fiber optic probe as illuminated through the tapered end and the non-tapered end. Two images as illuminated by shining light at varying angles into the tapered end of the fiber are shown.
Figure 3B:
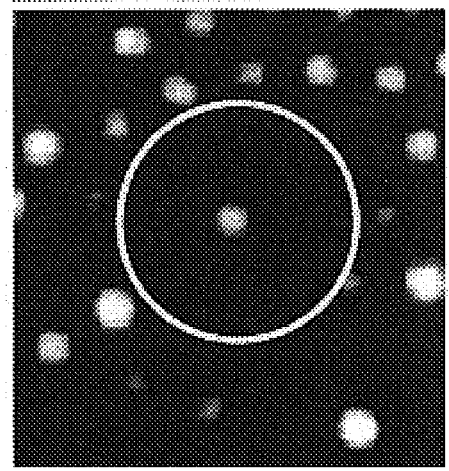

The light transmitted through the tapered fiber bundle was then imaged onto the digital camera, revealing that all of the individual fibers surrounding a single illuminated fiber element could be dark, thereby demonstrating no crosstalk between the fiber elements. This can be seen clearly in the marked fiber element shown in FIG. 3A. To ensure that the lack of light transmission in the surrounding fiber elements was not due to structural damage, the position of the diffuser was varied until each of the surrounding fiber elements also showed illumination (FIG. 3B).

Based on these analyses, it was found that no measurable cross talk occurs between fiber elements with diameters as small as 140 nm. This means that light collected from a 140 nm spot of a sample at the tapered tip of the imaging probe will be transmitted through only that fiber element until the light reaches the 4 μm untapered end. Thus, the image is magnified by a factor equivalent to the ratio of the size of the fiber elements on the untapered end to the tapered end, while also providing a large enough fiber element size to be imaged onto a CCD, ICCD or digital camera via conventional optics without degrading the resolution of the original image.

EXAMPLE 5

Imaging Capabilities of SERS Nano-imaging Probes

Demonstration of the imaging capabilities of these SERS nano-imaging probes was performed by fabricating several probes with only half of their tapered tip coated in silver. Once fabricated, the SERS active fiber tips were dipped into a $10^{-2}$ M solution of either benzoic acid or BCB. These two chemical species were chosen for their well characterized SERS spectra, as well as their different functional groups and, thus, for their SERS band positions. By using model species with different energy bands, it is possible to ensure that enhancements in signal are not related to analyte metal interactions and that the resulting enhancements, therefore, are not chemical dependant.

Figures 4A, 4B:
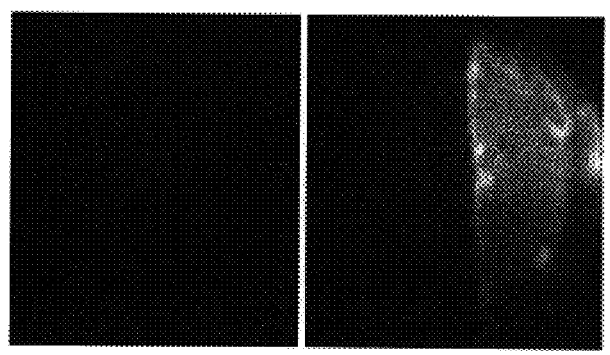
FIGS. 4A-4B demonstrate that an etched, tapered probe is effective in the nano-imaging system. SERS nano-imaging probe, with half of probe SERS active and imaged at 632.8 $cm^{-1}$ (FIG. 4A), and at 581.56 $cm^{-1}$ (FIG. 4B).

FIG. 4A corresponds to an image of a half silver coated fiber optic nano-imaging bundle that was coated with brilliant cresyl blue (BCB). This image is taken at a wavelength of 632.8 nm (0 cm$^{-1}$ shift) corresponding to the Rayleigh scatter line of the excitation laser. As expected, no image is present, as the notch filter has effectively removed the Rayleigh scattered light. In FIG. 4B, a SERS image of this same BCB coated fiber is shown, taken at a wavelength of 656.98 nm (581.56 cm$^{-1}$ shift), corresponding to a major Raman scatter band of the compound. In this image, the white semicircular shape on the right half of the image corresponds to the SERS emission from the BCB on the silver coated side of the nano-imaging probe. When compared to the background image in FIG. 4B, which was taken for the same acquisition time, it is clear that an excellent signal-to-background exists for SERS images obtained through these nano-imaging probes with individual fiber element diameters of 140 nm. In cases where 140 nm resolution is not required and larger individual fiber elements can be employed, the SERS image intensity increases significantly, until the size of the fiber is significantly greater than the diffraction limit of the light being imaged.

EXAMPLE 6

Uniformity of SERS Enhancement Factor

To provide uniform SERS enhancements across the surface of the nano-imaging probe, and thus chemical images directly related to the relative amount of each specific chemical of interest, it is important to ensure that the variability in surface roughness is kept to a minimum. Additionally, it is also important that the SERS enhancements at every location over the SERS active imaging area of these nano-imaging probes is large enough to allow for visualization of the small amount of analyte present in the light collection area of each individual fiber element, e.g., 140 nm. For probes with 140 nm spatial resolution, this corresponds to a circular area with a diameter of 12.12 μm, which is a relatively large image area compared to current scanning topographical techniques, e.g., atomic force microscopy or NSOM, with similar spatial resolutions.

To evaluate these parameters, several nano-imaging probes were fabricated with different spatial resolutions, i.e., fiber element diameters, ranging from 140 nm up to 1 µm. After etching with HF, the cladding spikes surrounding the cores' of the fiber elements were coated with silver, across the entire surface of the probe. These probes were then dipped into $10^{-2}$ M solutions of either benzoic acid or BCB and SERS images were obtained at several wavelengths, some corresponding to SERS bands of the molecule of interest and others corresponding to background wavelengths. Three such images can be seen in FIG. 5, with each frame A-C corresponding to a different fiber dipped in $10^{-2}$ M BCB and imaged at a wavelength corresponding to the major SERS band of the chemical at 580.00 cm$^{-1}$.

Figures 5A, 5B, 5C:
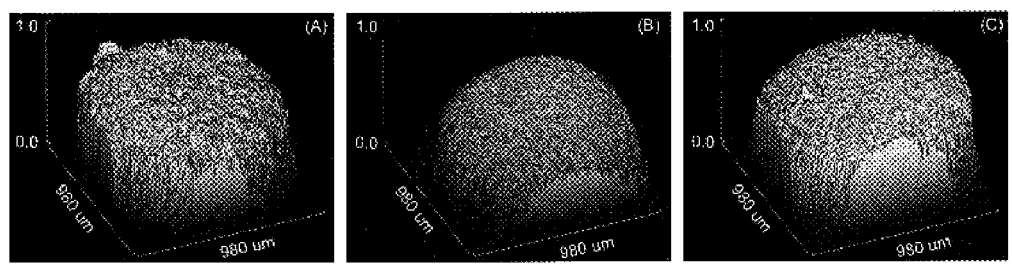
FIGS. 5A-5C show SERS images, corresponding the $10^{-2}$ M BCB peak at 580 $cm^{-1}$, of the distal end of etched probes converted to surface plots and normalized to 1.0. The surface of the probes in FIGS. 5A-5C are fairly uniform in nature, demonstrating relatively flat surface.

In FIG. 5 surface plots were constructed using ImageJ software and normalized to 1.0. Based upon the SERS signals produced at every location across the image of the probe when imaged using the nano-imaging system, it was found that the average relative standard deviation in surface enhancement across the surface of any individual nano-imaging probe was 1.94%, confirming the high degree of uniformity in SERS enhancement factor achieved by using a highly ordered underlying surface. In addition, to evaluating the variability across an individual probe's surface, the batch-to-batch variability in the fabrication of different fiber-optic nano-imaging probes can be seen from the differences between images in FIGS. 5A-5C. Upon analysis of the SERS signals obtained on the different nano-imaging probes, it was found that the relative standard deviation in SERS signals across all of the probes examined (n=6) was 3.16%.

EXAMPLE 7

SERS Nanoimaging Probe is Reusable Without a Loss of S/N Ratios

While a 3.16% standard deviation from nano-imaging fiber to nano-imaging fiber is acceptable for many applications in which multiple chemical images need to be taken, this may not always be the case. To avoid any variability that could be introduced through the use of multiple nano-imaging probes, it is possible to reuse an individual nano-imaging probe as many as 5 times, with minimal or no degradation in performance. Demonstration of this ability to wash and reuse these SERS nano-imaging probes can be seen from the SERS spectra in FIGS. 6A-6C, which were obtained from a SERS nano-imaging probe that was dipped into a solution of BCB, washed and re-dipped several times.

In FIG. 6A, the signal-to-noise ratio of the 580.00 cm$^{-1}$ band of the dye was calculated to be 260.00. Following this analysis, the fiber probe was immersed in water several times to remove any BCB adsorbed to the tip and a second spectrum was obtained from the element of the imaging bundle. The resulting spectrum from the washed probe tip can be seen in FIG. 6B. From this spectrum it can be seen that the SERS bands associated with BCB are no longer present. To verify that this was not due to degradation of the silver surface, e.g., by silver oxidation or scratching, the fiber probe was again dipped into the same $10^{-2}$ M solution of BCB, and another spectrum obtained from the same fiber element (see FIG. 6C). Again a signal noise ratio of 264.00 was found for the 580.00 cm$^{-1}$ band of the dye. This process was repeated several more times with no degradation or variation in the resulting SERS spectra for as many as 4 washes. This ability to reuse these fiber optic nano-imaging probes results in the ability to further reduce of the already small variability, i.e., RSD=1.94%, in SERS enhancement across an individual nano-imaging probe by allowing any images to be normalized to a previous image of a homogeneous sample obtained on the same probe.

EXAMPLE 8

SERS Nano-Imaging Probe Can Differentiate Between Chemicals

Figures 7A, 7B:
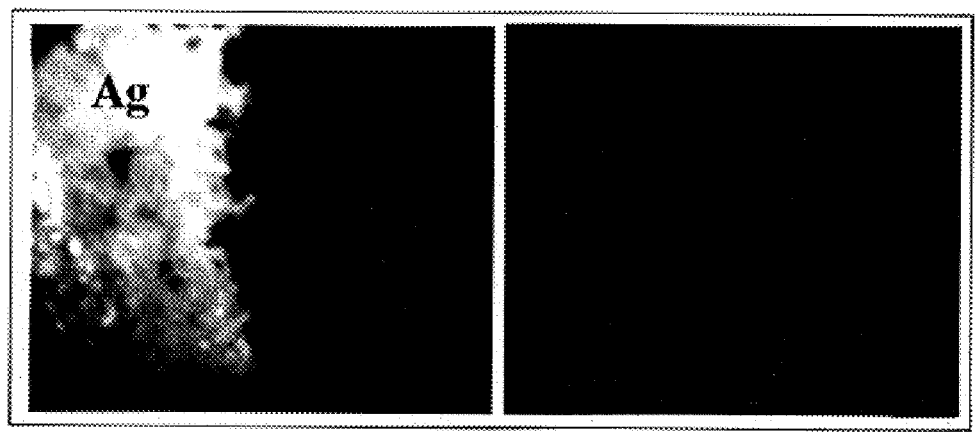

The nano-imaging probes are also capable of differentiating one chemical from another in a spatially resolved format, simply by varying the wavelength at which the scattered light is imaged. To validate this ability to differentiate the presence of one chemical from another, as well as the sensitivity of these nano-imaging probes, several drops of a dilute solution of BCB, i.e., $10^{-2}$ M, were added to one side of the silver coated probes and imaged at 656.00 nm, corresponding to the 580.00 cm$^{-1}$ band of the dye (FIG. 7A). From the image obtained it can be clearly seen that the half of the probe to which the dye was applied, i.e., left half of probe tip, is producing a strong signal in the 500 ms acquisition time employed. The signal-to-noise ratio of this image, in which each location being imaged corresponds to only a few molecules, demonstrates the high degree of sensitivity achieved with these nano-imaging probes. In addition, the non-uniform white areas, corresponding to the locations in which the dye was spotted onto the sample, demonstrates the ability of these probes to monitor the spatial distribution of a particular chemical, as well as it relative abundance at a particular location.

Following acquisition of the SERS image of the BCB spotted onto the nano-imaging probe, the tip was washed in water and allowed to dry before several drops of a $10^{-2}$ M solution of benzoic acid was placed on the same side of the probe that originally contained the BCB. After spotting with this relatively concentrated benzoic acid solution, a SERS image was once again acquired at 580.00 cm$^{-1}$ (FIG. 7B). However, since the benzoic acid has no SERS bands at this wavelength (FIG. 7D) like BCB (FIG. 7C) no image is obtained. To verify that this lack of signal was not due to the absence of benzoic acid or the degradation of the nano-imaging bundle, a series of other images were obtained at different wavelengths, corresponding to SERS active bands associated with benzoic acid, revealing the spatial distribution and relative quantity present at different locations. From the images in FIGS. 7A and 7B, it is clear that by choosing an appropriate wavelength for imaging, these SERS nano-imaging probes are capable of providing spatially resolved images of the presence of various chemical species, similar to the well established macroscopic imaging field.

THE FOLLOWING REFERENCES ARE CITED HEREIN

1. Li, et al. J. Am. Chem. Soc. 127, 14-15 (2004),
2. Liu, et al. J. Phys. Chem. B. 108, 20090-20094 (2004).
3. Maxwell, et al. J. Am. Chem. Soc. 124, 9606-9612 (2002).
4. Ai, et al. Biomacromolecules 3, 560-564 (2002).
5. Djalai, et al. J. Am. Chem. Soc. 126, 7935-7939 (2004).
6. P. B. Ruffin, SPIE Proc, 5359, 177-187 (2004).
7. Song, et al. Anal. Chem. 76, 2591-2595 (2004).
8. N. V. Kulagina and A. C. Micheal, Anal. Chem. 75, 4875-7881 (2003).
9. Dong, et al. Biochem. 42, 2768-2773 (2003).
10. H. Li, B. M. Cullum, SPIE Proc. 5261, 142-148 (2003).
11. Zeng, et al. Anal. Chem. 75, 6807-6812 (2003).

12. Brookner, et al. Photochem. and Photobio. 71, 730-736 (2000).
13. Vo-Dinh, et al. App. Spec. (1996).
14. Geniadecka, et al. J. Raman Spectrosc. 125-129 (1997).
15. M. G. Shim and B. C. Wilson. J. Raman Spectrosc. 28,131-142 (1997).
16. Redd, et al. App. Spec. 6, 787-791 (1993).
17. Buschman, et al., Anal. Chem. 3771-3775 (2000).
18. Hanlon et al., Phys. Med. Bio. 45, R1-R59 (2000).
19. Richards-Kortum, et al. Ann. Rev. Phys. Chem. 47, 555-606 (1996).
20. Mahadevan-Jansen, et al. Photochem. and Photobio. 69, 123-132 (1998).
21. Yang, et al. J. Raman Spectrosc. 29, 725-732 (1998).
22. S. Nie and S. R. Emory, Science 275, 1102-1106 (1997).
24. Kneipp, et al. Phys. Rev. Lett. 78, 1667-1670 (1997).
26. Betzig, et al. Science 251, 1468-1470 (1991).
27. E. Betzig and R. J. Chichester, Science 262, 1422-1425 (1993).
28. E. Betzig and K. J. Trautman, Science 257, 189-195 (1992).
29. Hecht, et al. J. App. Phys. 81, 2492-2498 (1997).
30. Schaller, et al. Anal. Chem. 72, 5361-5364 (2000).
31. Kwak, et al., Anal. Chem. 3257-3262 (2001).
32. C. M. Harris, Anal. Chem. 223A-228A (2003).
33. Kim, et al. Anal. Chem. 73 5984-5991 (2001).
34. Deckert, et al. Anal. Chem. 70, 2646-2650 (1998).
35. Zhang, et al. Langmuir 21, 520-523 (2005).
36. Hecht, et al. J. App. Phys. 84, 5873-5882 (1998).
37. P. Pantano and D. R. Walt, Chem. Mat. 8, 2832-2835 (1996).
38. Bernhard, et al. Anal. Chem. 73, 2484-2490 (2001).
39. J. R. Epstein and D. R. Walt, Chem. Soc. Rev. 32, 203-214 (2003).
40. B. M. Cullum, Encyc. Nanosci. and Nanotech., M. Dekker, Ed., 2757-2768 (2004).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A nano-imaging probe for a surface enhanced Raman spectrometer, comprising:
   a fiber optic imaging bundle having a proximal flat tapered end and a distal flat non-tapered end, said imaging bundle including a plurality of equi-diameter fiber optic elements, each of said fiber optic elements having a tapered etched end with a flat surface at the proximal end uniformly contacting an analyte, a non-tapered non-etched end surface at the distal end; and
   a surface enhanced Raman scattering-active metal means deposited onto the tapered etched flat surface at the proximal end.

2. The nano-imaging probe of claim 1, wherein said surface enhanced Raman scattering-active metal means comprises:
   fiber optic elements each consisting of a core material and a cladding material surrounding the core material; and
   a metal surface deposited onto said cladding material.

3. The nano-imaging probe of claim 2, wherein said core and cladding material are etched at the proximal tapered end surface thereby forming uniform cladding spikes around the etched core.

4. The nano-imaging probe of claim 2, wherein said metal surface is silver.

5. The nano-imaging probe of claim 2, wherein said core material is germanium (IV) oxide.

6. The nano-imaging probe of claim 2, wherein said cladding material comprises a silica.

7. The nano-imaging probe of claim 1, wherein said plurality of fiber optic elements is about 30,000.

8. The nano-imaging probe of claim 1, wherein said proximal flat tapered end of the fiber optic imaging bundle has a diameter of about 160 microns.

9. The nano-imaging probe of claim 1, wherein each tapered, etched fiber optic element end surface has an identical diameter of about 140 nm to about 1000 nm.

10. The nano-imaging probe of claim 1, wherein each non-tapered, non-etched fiber optic element surface has an identical diameter of about 4 microns.

11. A surface enhanced Raman spectroscopic nano-imager, comprising:
   a radiation source;
   the nano-imaging probe of claim 1;
   a detector for detecting Raman scattered radiation;
   a first set of optics for directing incident radiation from said source to the proximal end surfaces of the nano-imaging probe;
   a second set of optics for directing Raman radiation emitted from the distal end surfaces of the nano-imaging probe to said detector.

12. The SERS nano-imager of claim 11, further comprising:
   means for analyzing and displaying said detected Raman scattered radiation as a Raman spectral image.

13. The SERS nano-imager of claim 11, wherein said radiation source is a laser producing radiation with a wavelength of about 632 nm.

14. The SERS nano-imager of claim 11, wherein said detector is a charge coupled device, an intensified charge coupled device or a digital camera.

15. The SERS nano-imager of claim 11, wherein said first set of optics comprises a bandpass filter and a mirror operably disposed between the radiation source and the nano-imaging probe.

16. The SERS nano-imager of claim 11, wherein said second set of optics comprises a microscope objective, a holographic notch filter and an acousto-optic tunable filter operably disposed between the nano-imaging probe and the detector.

17. A method for performing surface-enhanced Raman spectral analysis of an analyte, comprising:
   providing the SERS nano-imaging probe of claim 1;
   bringing an analyte into effective contact with the nano-imaging probe;
   illuminating molecules comprising said analyte with radiation of a wavelength to produce Raman scattered radiation therefrom; and collecting said Raman scattered radiation transmitted through said nano-imaging probe for spectral analysis of the analyte.

18. The method of claim 17, further comprising:
generating a signature spectrum for the analyte based on the spectral analysis.

19. A method of establishing the presence of an analyte in a given sample comprising:
bringing an analyte into effective contact with surface enhanced Raman scattering nano-imaging probe of claim 1;
illuminating molecules comprising said analyte with radiation of a wavelength to produce Raman scattered radiation therefrom;
collecting said Raman scattered radiation transmitted through said nano-imaging probe for spectral analysis of the analyte; and
generating a signature spectrum for the analyte based on the spectral analysis
wherein, if the spectral signature of the sample matches the spectral signature of the analyte, the analyte is present in the sample.

20. A method of identifying one or more molecules in a sample in real time, comprising:
bringing an analyte into effective contact with surface enhanced Raman scattering nano-imaging probe of claim 1;
illuminating molecules comprising said analyte with radiation of a wavelength to produce Raman scattered radiation therefrom;
collecting said Raman scattered radiation transmitted through said nano-imaging probe for spectral analysis of the analyte; and
generating a signature spectrum for the analyte based on the spectral analysis and
repeating the method steps using a different illuminating wavelength for each molecule to be identified, wherein an immediate comparison of Raman spectral signatures identifies the one or more molecules in real time.

* * * * *